US010265337B2

(12) United States Patent
Fishman (10) Patent No.: US 10,265,337 B2
(45) Date of Patent: Apr. 23, 2019

(54) USE OF A3 ADENOSINE RECEPTOR AGONIST IN OSTEOARTHRITIS TREATMENT

(71) Applicant: CAN-FITE BIOPHARMA LTD., Petach Tikva (IL)

(72) Inventor: Pnina Fishman, Herzliya (IL)

(73) Assignee: CAN-FITE BIOPHARMA LTD., Petach Tikva (IL)

( * ) Notice: Subject to any disclaimer, the term of this patent is extended or adjusted under 35 U.S.C. 154(b) by 0 days.

(21) Appl. No.: 15/160,462

(22) Filed: May 20, 2016

(65) Prior Publication Data

US 2016/0263142 A1    Sep. 15, 2016

Related U.S. Application Data

(63) Continuation of application No. 11/632,897, filed as application No. PCT/IL2006/001374 on Nov. 29, 2006, now abandoned.

(60) Provisional application No. 60/740,631, filed on Nov. 30, 2005.

(51) Int. Cl.
| | | |
|---|---|---|
| *A01N 43/04* | (2006.01) | |
| *A61K 31/70* | (2006.01) | |
| *A61K 31/7076* | (2006.01) | |
| *A61K 31/00* | (2006.01) | |
| *A61K 31/519* | (2006.01) | |
| *A61K 9/00* | (2006.01) | |
| *A61K 31/706* | (2006.01) | |
| *A61K 45/06* | (2006.01) | |

(52) U.S. Cl.
CPC ........ *A61K 31/7076* (2013.01); *A61K 9/0053* (2013.01); *A61K 31/00* (2013.01); *A61K 31/519* (2013.01); *A61K 31/706* (2013.01); *A61K 45/06* (2013.01)

(58) Field of Classification Search
None
See application file for complete search history.

(56) References Cited

U.S. PATENT DOCUMENTS

| 5,773,423 A | 6/1998 | Jacobson et al. |
| 2004/0167094 A1 | 8/2004 | Fishman |
| 2008/0051365 A1 | 2/2008 | Fishman et al. |

FOREIGN PATENT DOCUMENTS

| EP | 1 739 097 A1 | 1/2007 |
| JP | 2004-135657 A | 5/2004 |
| WO | 2004/045627 A1 | 6/2004 |
| WO | 2004/078184 A1 | 9/2004 |
| WO | 2004/079329 A2 | 9/2004 |
| WO | 2005/000331 A2 | 1/2005 |
| WO | 2005/095464 A1 | 10/2005 |
| WO | 2006/048884 A1 | 5/2006 |
| WO | 2006/059328 A1 | 6/2006 |

OTHER PUBLICATIONS

Martel-Pelletier Osteoarthritis and Cartilage (1998), vol. 6, pp. 374-376.*
Amin Osteoarthritis and Cartilage (1999), vol. 7, pp. 392-394.*
Chen et al. Bone Research (2017), vol. 5, 16044; pp. 1-13.*
Moretti et al. (2008) Extracorporeal shock waves down-regulate the expression of interleukin-10 and tumor necrosis factor-alpha in osteoarthritic chondrocytes. BMC Musculoskeletal Disorders, vol. 9.
Xu et al. (2009) Effect of electroacupuncture on the level of IL-1β and TNF-α in patients with osteoarthritis. Zhongguo Zhenjiu, vol. 29, No. 7, p. 529-531.
Sokolove et al. (2013) Role of inflammation in the pathogenesis of osteoarthritis: latest findings and interpretations. Therapeutic Advances in Musculoskeletal Disease, vol. 5, No. 2, p. 77-94.
Gotlieb (2005) Treatment of Rheumatoid Arthritis and Osteoarthritis. Retrieved [online] from the internet <http://www.arthritis.co.za/treatment_of_rheumatoid_arthriti.html> Retrieved on Sep. 25, 2014.
McWhinney et al. (1996) Activation of adenosine A3 receptors on macrophages inhibits tumor necrosis factor-α European Journal of Pharmacology, vol. 310, p. 209-216.
Szabó et al. (1998) Suppression of macrophage inflammatory protein (MIP)-1α production and collagen-induced arthritis by adenosine receptor agonists. British Journal of Pharmacology, vol. 125, p. 379-387.
Liu et al. (2003) The role of apoptosis in rheumatoid arthritis. Current Opinion in Pharmacology, vol. 3, p. 317-322.
Goodman and Gilman's The Pharmacological Basis of Therapeutics. editors Joel G. Hardman and Lee E. Limbird, published by The McGraw-Hill Companies, Inc., 2001, p. 3-8.
Definition of "prevent" from the Merriam Webster Online Dictionary [online], [Retrieved on Aug. 15, 2008]. Retrieved from the internet <http://www.merriam-webster.com/cgi-bin/dictionary?book=Dictionary&va=prevent>.
"What is Osteoarthritis?" by U.S. Department of Health and Human Services, National Institute of Health, National Institute of Arthritis and Musculoskeletal and Skin Diseases, Sep. 2006.

(Continued)

*Primary Examiner* — Patrick T Lewis
(74) *Attorney, Agent, or Firm* — Vorys, Sater, Seymour and Pease LLP (57) ABSTRACT

Provided is an $A_3$ adenosine receptor agonist ($A_3AR$ agonist) for the preparation of a pharmaceutical composition for the treatment of a mammal subject having osteoarthritis (OA), as well as to a method for the treatment of OA in a mammal subject, the method includes administering to said subject in need of said treatment an amount of $A_3AR$ agonist, the amount being effective to treat or prevent the development of OA. Preferred but not exclusive $A_3AR$ agonists in accordance with the present subject matter are IB-MECA and Cl-IB-MECA. The $A_3AR$ agonist may be administered in combination with another drug, such as Methotrexate (MTX). Also provided are pharmaceutical compositions for treatment of osteoarthritis including an amount of an $A_3AR$ agonist.

13 Claims, 3 Drawing Sheets

(56) References Cited

OTHER PUBLICATIONS

Fernandes et al., "The role of cytokines in osteoarthritis pathophysiology", Biorheology, vol. 39, pp. 237-246, (2002).

Baharav et al., "Antiinflammatory Effect of A3 Adenosine Receptor Agonists in Murine Autoimmune Arthritis Models", J Rheumatol, vol. 32, pp. 469-476, (2005).

Mabley et al., "The A3 adenosine agonist, IB-MECA, protects against the development of arthritis and reverses established arthritis", Experimental Biology 2002: Meeting Abstracts, Abstract 759.5, p. A1044, (2002).

Ichikawa et al., "Current conditions and issue of methotrexate therapy for chronic articular rheumatism", Weekly History of Medicine, vol. 182, Issue 9, pp. 642-646, (1997). with English language summary.

Neidel et al. "The effects of high-dose methotrexate on the development of cartilage lesions in a lapine model of osteoarthrosis". Archives of Orthopaedic and Trauma Surgery. 1998, vol. 117, pp. 265-269. Springer-Verlag.

Montesinos et al., "Suppression of inflammation by low-dose methotrexate is mediated by adenosine A2A receptor but not A3 receptor activation in thioglycollate-induced peritonitis", Arthritis Research & Therapy, vol. 8, No. R53, Six pages, (2006).

Ochaion et al., "Methotrexate enhances the anti-inflammatory effect of CF101 via up-regulation of the A3 adenosine receptor expression", Arthritis Research & Therapy, vol. 8, pp. 1-12, (2006).

Jacobson et al. "A3 Adenosine receptor agonists: history and future perspectives". "4" In: Pier Andrea Borea: "A3 adenosine receptors from cell biology to pharmacology and therapeutics". pp. 93-120. Springer (2010).

* cited by examiner

Figure 3A  Figure 3B  Control

Figure 3C  Figure 3D  CF101

USE OF A3 ADENOSINE RECEPTOR AGONIST IN OSTEOARTHRITIS TREATMENT

This is a Continuation Application of U.S. patent application Ser. No. 11/632,897, filed on Jan. 19, 2007, which was a National Phase Application filed under 35 U.S.C. § 371 as a national stage of PCT/IL2006/001374, filed on Nov. 29, 2006, an application claiming the benefit under 35 U.S.C. § 119(e) of U.S. Provisional Application No. 60/740,631, filed on Nov. 30, 2005, the content of each of which is hereby incorporated by reference in their entirety.

FIELD OF THE INVENTION

This invention relates to therapy and in particular to treatment of osteoarthritis.

BACKGROUND OF THE INVENTION

Osteoarthritis, known in the past as degenerative arthritis, is the most common form of arthritis. It is a joint disease that occurs after abnormality or damage of joints or without joint damage. The disease involves the deterioration of cartilage in the joints. Over time, the cartilage, covering the ends of bones in a joint, begins to break down and may wear away entirely, and the bones will rub together, causing pain. Due to pain in a joint, the surrounding muscle is used less, and muscle strength is thus weakened.

The usual symptoms of osteoarthritis are stiffness, limitation of motion, pain and joint deformity and affected joints display edema, hot flashes and abnormal enlargement of joints.

The prevalence of osteoarthritis is similar in men and women. However, in women a greater number of joints are affected, while men suffer from a higher frequency of hip joint invasion. The risk factors of osteoarthritis include aging (prevalence rates increase markedly with age), obesity, congenital dysplasia of the hip, accidental or athletic trauma, a history of arthritis, drugs, particular job groups, surgery and heredity. Osteoarthritis itself does not greatly affect one's life, but chronic osteoarthritis sustaining for a long period of time causes pain and deformity of the joints and thus reduces the quality of life. In particular, osteoarthritis in the knees is known as a major cause of chronic disability.

Various drugs and treatment methods have been developed and used for the treatment of osteoarthritis. The main goals of the treatment are to relieve pain, maintain the functions of the joints and prevent disability due to the functional disorder of the joints.

Currently there is no known medical treatment to reverse the effects of this cartilage damage. Rather the therapies for osteoarthritis are directed mainly towards treating the symptoms. In this regard, osteoarthritis has been treated using anti-inflammatory substances of the corticosteroid type (such as hydrocortisone and Betamethasone), which function to inhibit prostaglandin synthesis, as well as with a large number of nonsteroidal anti-inflammatory drugs (NSAIDs, such as diclofenac, aspirin and ibuprofen), which have an analgesic as well anti-inflammatory effect. However, due to their serious side effects, these drugs are used with special caution.

Thus, there is a continuous need to search and develop new methods for treating osteoarthritis.

SUMMARY OF THE INVENTION

The invention provides the use of an $A_3$ adenosine receptor agonist ($A_3AR$ agonist) for the preparation of a pharmaceutical composition for the treatment of osteoarthritis in a mammal subject.

Further, the present invention provides a method for the treatment of osteoarthritis in a mammal subject, the method comprises administering to said subject in need of said treatment an amount of an $A_3AR$ agonist, the amount being effective to treat or prevent the development of osteoarthritis.

Yet further, the invention provides a pharmaceutical composition for the treatment of osteoarthritis in a mammal subject comprising as active ingredient an $A_3AR$ agonist and a pharmaceutically acceptable carrier.

The therapeutic use of an $A_3AR$ agonist may be by itself, or at times in combination with other drugs such as methotrexate (MTX), steroids, NSAIDS, and others.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF EXEMPLARY EMBODIMENTS

The invention is described in the following detailed description with reference to therapeutic methods for the treatment of osteoarthritis involving administration of an $A_3AR$ agonist to a subject in need of same. It should be noted that in addition to said therapeutic methods, also encompassed within the present invention is the use of an $A_3AR$ agonist for the preparation of a pharmaceutical composition for administration to a subject suffering from osteoarthritis as well as a pharmaceutical composition for the treatment of osteoarthritis that comprises an effective amount of an $A_3AR$ agonist and a pharmaceutically acceptable carrier.

As used in the specification and claims, the forms "a", "an" and "the" include singular as well as plural references unless the context clearly dictates otherwise. For example, the term "an $A_3AR$ agonist" includes one or more agonists.

Further, as used herein, the term "comprising" is intended to mean that the methods or composition includes the recited elements, but not excluding others. Similarly, "consisting essentially of" is used to define methods and compositions that include the recited elements but exclude other elements that may have an essential significance therapeutic activity towards osteoarthritis. For example, a composition consisting essentially of an $A_3AR$ agonist will not include or include only insignificant amounts (amounts that will have an insignificant effect on osteoarthritis) of other active ingredients that have such an activity. Also, a composition consisting essentially of the $A_3AR$ agonist as defined herein would not exclude trace contaminants from the isolation and purification method, pharmaceutically acceptable carriers, such as phosphate buffered saline, excipients, preservatives, and the like. "Consisting of" shall mean excluding more than trace elements of other elements. Embodiments defined by each of these transition terms are within the scope of this invention.

Further, all numerical values, e.g., concentration or dose or ranges thereof, are approximations which are varied (+) or (−) by up to 20%, at times by up to 10% of from the stated values. It is to be understood, even if not always explicitly stated that all numerical designations are preceded by the term "about". It also is to be understood, although not always explicitly stated, that the reagents described herein are merely exemplary and that equivalents of such are known in the art.

There is provided by the present invention a method for treatment of osteoarthritis in a mammal subject having osteoarthritis, the method comprises administering to said subject an effective amount of an $A_3AR$ agonist.

In the context of the present invention the term "treatment" comprises treating osteoarthritis to reverse diseases symptoms, preventing the development of osteoarthritis, as well as managing and/or ameliorating osteoarthritis or one or more symptoms thereof. Thus, treatment refers to administering a therapeutically effective amount of an $A_3AR$ agonist to achieve a desired therapeutic effect. The desired therapeutic effect may include, without being limited thereto, improving motility of the subject, decrease in swelling and tenderness of the joints, slowing or preventing the deterioration of the joints and the surrounding tissue, slowing any irreversible damage caused by a chronic stage of osteoarthritis, increasing the time period of the remission between acute attacks of the disease, lessening of the severity of or curing osteoarthritis, or providing more rapid recovery form osteoarthritis, as well as decreasing any one of the following symptoms: stiffness, pain and joint deformity, joint edema, hot flashes and abnormal enlargement of joints or preventing the manifestation of such symptoms before they occur.

In the context of the present invention treatment also includes prevention of the development of osteoarthritis (e.g. in subjects having high disposition of developing the disease, such as athletes) as well as reversal of damage caused to cartilage as a result of the disease.

As to the $A_3AR$ agonist, such compounds are known in the art and are readily available. Generally, the $A_3AR$ agonist is any compound that is capable of specifically binding to the adenosine $A_3$ receptor ("$A_3R$"), thereby fully or partially activating said receptor thereby yielding a therapeutic effect (in this particular case, an anti-osteoarthritic effect). The $A_3AR$ agonist is thus a molecule that exerts its prime effect through the binding and activation of the $A_3AR$. This means that at the doses it is being administered it essentially binds to and activates only the $A_3R$. In a preferred embodiment, the $A_3AR$ agonist has a binding affinity ($K_i$) to the human $A_3AR$ of less than 1000 nM, desirably less than 500 nM, advantageously less 200 nM and even less than 100 nM, typically less than 50 nM, preferably less than 20 nM, more preferably less than 10 nM and ideally less than 5 nM. The lower the $K_i$, the lower the dose of the $A_3AR$ agonist (that may be used) that will be effective in activating the $A_3R$ and thus achieving a therapeutic effect.

It should be noted that some $A_3AR$ agonists can also interact with and activate other receptors with lower affinities (namely a higher Ki). A molecule will be considered an $A_3AR$ agonists in the context of the invention (namely a molecule that exerts its prime effect through the binding and activation $A_3R$) if its affinity to the $A_3R$ is at least 3 times (i.e. its Ki to the $A_3R$ is at least 3 times lower), preferably 10 times, desirably 20 times and most preferably at least 50 times larger than the affinity to any other of the adenosine receptors.

The affinity of $A_3AR$ agonists to the human $A_3R$ as well as its relative affinity to the other human adenosine receptors can be determined by a number of assays, such as a binding assay. Examples of binding assays include providing membranes or cells having the receptor and measuring the ability of the $A_3AR$ agonist to displace a bound radioactive agonist; utilizing cells that display the respective human adenosine receptor and measuring, in a functional assay, the ability of the $A_3AR$ agonist to activate or deactivate, as the case may be, downstream signaling events such as the effect on adenylate cyclase measured through increase or decrease of the cAMP level; etc. Clearly, if the administered level of an $A_3AR$ agonist is increased such that its blood level reaches a level approaching that of the Ki of the other adenosine receptors, activation of these receptors may occur following such administration, in addition to activation of the $A_3R$. An $A_3AR$ agonist is thus preferably administered at a dose such that the blood level that will be attained will give rise to essentially only $A_3R$ activation.

The characteristic of some adenosine $A_3AR$ agonists and methods of their preparation are described in detail in, inter alia, U.S. Pat. No. 5,688,774; U.S. Pat. No. 5,773,423; U.S. Pat. No. 5,573,772; U.S. Pat. No. 5,443,836; U.S. Pat. No. 6,048,865; WO 95/02604; WO 99/20284; WO 99/06053; WO 97/27173 and WO 01/19360, all of which are incorporated herein by reference.

The following examples are specified in U.S. Pat. No. 5,688,774 at column 4, lines 67-column 6, line 16; column 5, lines 40-45; column 6, lines 21-42; column 7, lines 1-11; column 7, lines 34-36; and column 7, lines 60-61:

$N^6$-(3-iodobenzyl)-9-methyladenine;
$N^6$-(3-iodobenzyl)-9-hydroxyethyladenine;
R—$N^6$-(3-iodobenzyl)-9-(2,3-dihydroxypropyl)adenine;
S—$N^6$-(3-iodobenzyl)-9-(2,3-dihydroxypropyl)adenine;
$N^6$-(3-iodobenzyladenin-9-yl)acetic acid;
$N^6$-(3-iodobenzyl)-9-(3-cyanopropyl)adenine;
2-chloro-$N^6$-(3-iodobenzyl)-9-methyladenine;
2-amino-$N^6$-(3-iodobenzyl)-9-methyladenine;
2-hydrazido-$N^6$-(3-iodobenzyl)-9-methyladenine;
$N^6$-(3-iodobenzyl)-2-methylamino-9-methyladenine;
2-dimethylamino-$N^6$-(3-iodobenzyl)-9-methyladenine;
$N^6$-(3-iodobenzyl)-9-methyl-2-propylaminoadenine;
2-hexylamino-$N^6$-(3-iodobenzyl)-9-methyladenine;
$N^6$-(3-iodobenzyl)-2-methoxy-9-methyladenine;
$N^6$-(3-iodobenzyl)-9-methyl-2-methylthioadenine;
$N^6$-(3-iodobenzyl)-9-methyl-2-(4-pyridylthio)adenine;
(1S, 2R, 3S, 4R)-4-(6-amino-2-phenylethylamino-9H-purin-9-yl)cyclopentane-1,2,3-triol;

(1S, 2R, 3S, 4R)-4-(6-amino-2-chloro-9H-purin-9-yl) cyclopentane-1,2,3-triol;
(±)-9-[2α,3α-dihydroxy-4β-(N-methylcarbamoyl)cyclopent-1β-yl)]-N⁶-(3-iodobenzyl)-adenine;
2-chloro-9-(2'-amino-2',3'-dideoxy-β-D-5'-methyl-arabino-furanamido)-N⁶-(3-iodobenzyl)adenine;
2-chloro-9-(2',3'-dideoxy-2'-fluoro-β-D-5'-methyl-arabino furanamido)-N⁶-(3-iodobenzyl)adenine;
9-(2-acetyl-3-deoxy-β-D-5-methyl-ribofuronamido)-2-chloro-N⁶(3-iodobenzyl)adenine;
2-chloro-9-(3-deoxy-2-methanesulfonyl-β-D-5-methyl-ribofuronamido)-N⁶-(3-iodobenzyl)adenine;
2-chloro-9-(3-deoxy-β-D-5-methyl-ribofuronamido)-N⁶-(3-iodobenzyl)adenine;
2-chloro-9-(3,5-1,1,3,3-tetraisopropyldisiloxyl-β-D-5-ribofuranosyl)-N⁶-(3-iodobenzyl)adenine;
2-chloro-9-(2',3'-O-thiocarbonyl-β-D-5-methyl-ribofuranamido)-N⁶-(3-iodobenzyl)adenine;
9-(2-phenoxythiocarbonyl-3-deoxy-β-D-5-methyl-ribofuronamido)-2-chloro-N⁶-(3-iodobenzyl)adenine;
1-(6-benzylamino-9H-purin-9-yl)-1-deoxy-N,4-dimethyl-β-D-ribofuranosiduronamide;
2-chloro-9-(2,3-dideoxy-β-D-5-methyl-ribofuronamido)-N⁶ benzyladenine;
2-chloro-9-(2'-azido-2',3'-dideoxy-β-D-5'-methyl-arabino-furanamido)-N⁶-benzyladenine;
2-chloro-9-β-D-erythrofuranoside)-N⁶-(3-iodobenzyl)adenine;
N⁶-(benzodioxanemethyl)adenosine;
1-(6-furfurylamino-9H-purin-9-yl)-1-deoxy-N-methyl-β-D-ribofuranosiduronamide;
N⁶-[3-(L-prolylamino)benzyl]adenosine-5'-N-methyluronamide;
N⁶-[3-(β-alanylamino)benzyl]adenosine-5'-N-methyluronamide;
N⁶-[3-(N-T-Boc-β-alanylamino)benzyl]adenosine-5'-N-methyluronamide;
6-(N'-phenylhydrazinyl)purine-9-β-ribofuranoside-5'-N-methyluronamide;
6-(O-phenylhydroxylamino)purine-9-β-ribofuranoside-5'-N-methyluronamide;
9-(β-D-2',3'-dideoxyerythrofuranosyl)-N⁶-[(3-β-alanylamino)benzyl]adenosine;
9-(β-D-erythrofuranoside)-2-methylamino-N⁶-(3-iodobenzyl)adenine;
2-chloro-N-(3-iodobenzyl)-9-(2-tetrahydrofuryl)-9H-purin-6-amine;
2-chloro-(2'-deoxy-6'-thio-L-arabinosyl)adenine; and
2-chloro-(6'-thio-L-arabinosyl)adenine.

In U.S. Pat. No. 5,773,423 at column 6, line 39, to column 7, line 14, specifically disclosed are compounds which include the formula:

wherein
$X_1$ is $R^aR^bNC(=O)$, wherein $R^a$ and $R^b$ may be the same or different and are selected from the group consisting of hydrogen, $C_1$-$C_{10}$ alkyl, amino, $C_1$-$C_{10}$ haloalkyl, $C_1$-$C_{10}$ aminoalkyl, and $C_3$-$C_{10}$ cycloalkyl;

$R_2$ is selected from the group consisting of hydrogen, halo, $C_1$-$C_{10}$ alkyoxy, amino, $C_2$-$C_{10}$ alkenyl, and $C_2$-$C_{10}$ alkynyl; and $R_5$ is selected from the group consisting of R— and S-1-phenylethyl, an unsubstituted benzyl group, and a benzyl group substituted in one or more positions with a substituent selected from the group consisting of $C_1$-$C_{10}$ alkyl, amino, halo, $C_1$-$C_{10}$ haloalkyl, nitro, hydroxy, acetamido, $C_1$-$C_{10}$ alkoxy, and sulfo.

More specific compounds include those of the above formula wherein $R^a$ and $R^b$ may be the same or different and are selected from the group consisting of hydrogen and $C_1$-$C_{10}$ alkyl, particularly when $R_2$ is hydrogen or halo, especially hydrogen.

Additional specific compounds are those compounds wherein $R^a$ is hydrogen and $R_2$ is hydrogen, particularly when $R_5$ is unsubstituted benzyl.

More specific compounds are such compounds wherein $R^b$ is a $C_1$-$C_{10}$ alkyl or $C_3$-$C_{10}$ cycloalkyl, particularly a $C_1$-$C_{10}$ alkyl, and more particularly methyl.

Especially specific are those compounds where $R^a$ is hydrogen, $R^b$ is $C_1$-$C_{10}$ alkyl or $C_3$-$C_{10}$ cycloalkyl, and $R_5$ is R— or S-1-phenylethyl or a benzyl substituted in one or more positions with a substituent selected from the group consisting of halo, amino, acetamido, $C_1$-$C_{10}$ haloalkyl, and sulfo, where the sulfo derivative is a salt, such as a triethylammonium salt.

An example of an especially preferred compound disclosed in U.S. Pat. No. 5,773,423 is IB-MECA. In addition, those compounds in which $R_2$ is a $C_2$-$C_{10}$ alkenylene of the formula $R^d$—C=C— where $R^d$ is a $C_1$-$C_8$ alkyl are particularly noted in this publication. Also specific are those compounds wherein $R_2$ is other than hydrogen, particularly those wherein $R_2$ is halo, $C_1$-$C_{10}$ alkylamino, or $C_1$-$C_{10}$ alkylthio, and, more preferably, when additionally $R^a$ is hydrogen, $R^b$ is a $C_1$-$C_{10}$ alkyl, and/or $R_5$ is a substituted benzyl.

Such specifically disclosed compounds include 2-chloro-N⁶-(3-iodobenzyl)-9-[5-(methylamido)-β-D-ribofuranosyl]-adenine, N⁶-(3-iodobenzyl)-2-methylamino-9-[5-(methylamido)-β-D-ribofuranosyl]-adenine, and N⁶-(3-iodobenzyl)-2-methylthio-9-[5-(methylamido)-β-D-ribofuranosyl]-adenine.

Further U.S. Pat. No. 5,773,423 discloses at column 7, line 60, through column 8, line 6, $A_3AR$ agonists as modified xanthine-7-ribosides having the formula:

wherein

X is O;

$R_6$ is $R^aR^bNC(=O)$, wherein $R^a$ and $R^b$ may be the same or different and are selected from the group consisting of hydrogen, $C_1$-$C_{10}$ alkyl, amino, $C_1$-$C_{10}$ haloalkyl, $C_1$-$C_{10}$ aminoalkyl, and $C_3$-$C_{10}$ cycloalkyl;

$R_7$ and $R_8$ may be the same or different and are selected from the group consisting of $C_1$-$C_{10}$ alkyl, R— and S-1-phenylethyl, an unsubstituted benzyl group, and a benzyl group substituted in one or more positions with a substituent selected from the group consisting of $C_1$-$C_{10}$ alkyl, amino, halo, $C_1$-$C_{10}$ haloalkyl, nitro, hydroxy, acetamido, $C_1$-$C_{10}$ alkoxy, and sulfo; and $R_9$ is selected from the group consisting of halo, benzyl, phenyl, and $C_3$-$C_{10}$ cycloalkyl.

WO 99/06053 discloses in examples 19-33 compounds selected from:

$N^6$-(4-biphenyl-carbonylamino)-adenosine-5'-N-ethyluronamide;

$N^6$-(2,4-dichlorobenzyl-carbonylamino)-adenosine-5'-N-ethyluronamide;

$N^6$-(4-methoxyphenyl-carbonylamino)-adenosine-5'-N-ethyluronamide;

$N^6$-(4-chlorophenyl-carbonylamino)-adenosine-5'-N-ethyluronamide;

$N^6$-(phenyl-carbonylamino)-adenosine-5'-N-ethyluronamide;

$N^6$-(benzylcarbamoylamino)-adenosine-5'-N-ethyluronamide;

$N^6$-(4-sulfonamido-phenylcarbamoyl)-adenosine-5'-N-ethyluronamide;

$N^6$-(4-acetyl-phenylcarbamoyl)-adenosine-5'-N-ethyluronamide;

$N^6$-((R)-α-phenylethylcarbamoyl)-adenosine-5'-N-ethyluronamide;

$N^6$-((S)-α-phenylethylcarbamoyl)-adenosine-5'-N-ethyluronamide;

$N^6$-(5-methyl-isoxazol-3-yl-carbamoyl)-adenosine-5'-N-ethyluronamide;

$N^6$-(1,3,4-thiadiazol-2-yl-carbamoyl)-adenosine-5'-N-ethyluronamide;

$N^6$-(4-n-propoxy-phenylcarbamoyl)-adenosine-5'-N-ethyluronamide;

$N^6$-bis-(4-nitrophenylcarbamoyl)-adenosine-5'-N-ethyluronamide; and $N^6$-bis-(5-chloro-pyridin-2-yl-carbamoyl)-adenosine-5'-N-ethyluronamide.

According to one embodiment of the invention, the $A_3AR$ agonist is a compound that exerts its prime effect through the binding and activation of the adenosine $A_3AR$ and is a purine derivative falling within the scope of the general formula (I):

(I)

wherein, $R_{11}$ represents an alkyl, hydroxyalkyl, carboxyalkyl or cyanoalkyl or a group of the following general formula (II):

(II)

in which:

Y represents oxygen, sulfur or $CH_2$;

$X_{11}$ represents H, alkyl, $R^eR^fNC(=O)$— or $HOR^g$—, wherein
  $R^e$ and $R^f$ may be the same or different and are selected from the group consisting of hydrogen, alkyl, amino, haloalkyl, aminoalkyl, BOC-aminoalkyl, and cycloalkyl or are joined together to form a heterocyclic ring containing two to five carbon atoms; and
  $R^g$ is selected from the group consisting of alkyl, amino, haloalkyl, aminoalkyl, BOC-aminoalkyl, and cycloalkyl;

$X_{12}$ is H, hydroxyl, alkylamino, alkylamido or hydroxyalkyl;

$X_{13}$ and $X_{14}$ represent independently hydrogen, hydroxyl, amino, amido, azido, halo, alkyl, alkoxy, carboxy, nitrilo, nitro, trifluoro, aryl, alkaryl, thio, thioester, thioether, —OCOPh, —OC(=S)OPh or both $X_{13}$ and $X_{14}$ are oxygens connected to >C=S to form a 5-membered ring, or $X_{12}$ and $X_{13}$ form the ring of formula (III):

(III)

where R' and R" represent independently an alkyl group;

$R_{12}$ is selected from the group consisting of hydrogen, halo, alkylether, amino, hydrazido, alkylamino, alkoxy, thioalkoxy, pyridylthio, alkenyl; alkynyl, thio, and alkylthio; and $R_{13}$ is a group of the formula —$NR_{15}R_{16}$ wherein $R_{15}$ is a hydrogen atom or a group selected from alkyl, substituted alkyl or aryl-NH—C(Z)—, with Z being O, S, or $NR^a$ with $R^e$ having the above meanings; wherein when $R_{15}$ is hydrogen than

$R_{16}$ is selected from the group consisting of R— and S-1-phenylethyl, benzyl, phenylethyl or anilide groups unsubstituted or substituted in one or more positions with a substituent selected from the group consisting of alkyl, amino, halo, haloalkyl, nitro, hydroxyl, acetoamido, alkoxy, and sulfonic acid or a salt thereof; benzodioxanemethyl, fururyl, L-propylalanyl-aminobenzyl, β-alanylamino-benzyl, T-BOC-β-alanylaminobenzyl, phenylamino, carbamoyl, phenoxy or cycloalkyl; or $R_{16}$ is a group of the following formula:

or when $R_{15}$ is an alkyl or aryl-NH—C(Z)—, then, $R_{16}$ is selected from the group consisting of heteroaryl-$NR^a$—C (Z)—, heteroaryl-C(Z)—, alkaryl-NR$^a$—C(Z)—, alkaryl-C (Z)—, aryl-NR—C(Z)— and aryl-C(Z)—; Z representing an oxygen, sulfor or amine; or a physiologically acceptable salt of the above compound.

According to one preferred embodiment, the $A_3AR$ agonist is a nucleoside derivative of the general formula (IV):

(IV)

wherein $X_1$, $R_2$ and $R_5$ are as defined above, and physiologically acceptable salts of said compound.

The non-cyclic carbohydrate groups (e.g. alkyl, alkenyl, alkynyl, alkoxy, aralkyl, alkaryl, alkylamine, etc) forming part of the substituent of the compounds of the present invention are either branched or unbranched, preferably containing from one or two to twelve carbon atoms.

A specific group of A3AR agonists are the $N^6$-benzyladenosine-5'-uronamide derivatives. Some preferred $N^6$-benzyladenosine-5'-uronamide derivatives are $N^6$-2-(4-aminophenyl)ethyladenosine (APNEA), $N^6$-(4-amino-3-iodobenzyl)adenosine-5'-(N-methyluronamide) (AB-MECA) and 1-deoxy-1-{6-[({3-iodophenyl} methyl) amino]-9H-purine-9-yl}-N-methyl-β-D-ribofuranuronamide (IB-MECA) and 2-chloro-$N^6$-(3-iodobenzyl)adenosine-5'-N-methlyuronamide (Cl-IB-MECA).

According to another embodiment, the $A_3AR$ agonist may be an oxide derivative of adenosine, such as $N^6$-benzyladenosine-5'N-alkyluronamide-$N^1$-oxide or $N^6$-benzyladenosine-5'-N-dialkyluronamide-$N^1$-oxide, wherein the 2-purine position may be substituted with an alkoxy, amino, alkenyl, alkynyl or halogen The $A_3AR$ agonist is administered in amounts which are sufficient to achieve an anti-osteoarthritic effect. As will be appreciated, the amount of the $A_3AR$ agonist will depend on the severity of the disease, the intended therapeutic regiment and the desired therapeutic dose. By way of example, were the dose is 1 mg per day and the desired administration regiment is once daily administration, the amount of the $A_3AR$ agonist in a pharmaceutical composition comprising same will be 1 mg. Where it is intended to divide this daily dose in 2 daily administrations, the amount of the active agent in the pharmaceutical composition will be 0.5 mg.

An amount effective to achieve the desired effect is determined by considerations known in the art. An "anti-osteoarthritic effective amount" for purposes herein must be effective to achieve a therapeutic effect, the therapeutic effect being as defined hereinbefore.

It is appreciated that the effective amount depends on a variety of factors including the affinity of the chosen $A_3AR$ agonist to the $A_3AR$, its distribution profile within the body, a variety of pharmacological parameters such as half life in the body, on undesired side effects, if any, on factors such as age and gender of the subject to be treated, etc. The effective amount is typically tested in clinical studies having the aim of finding the effective dose range, the maximal tolerated dose and the optimal dose. The manner of conducting such clinical studies is well known to a person versed in the art of clinical development.

An amount may also at times be determined based on amounts shown to be effective in animals. It is well known that an amount of X mg/Kg administered to rats can be converted to an equivalent amount in another species (notably humans) by the use of one of possible conversions equations well known in the art. Examples of conversion equations are as follows:

Conversion I:

| Species | Body Wt. (Kg) | Body Surf. Area (m$^2$) | Km Factor |
|---|---|---|---|
| Mouse | 0.2 | 0.0066 | 3.0 |
| Rat | 0.15 | 0.025 | 5.9 |
| Human Child | 20.0 | 0.80 | 25 |
| Adult | 70.0 | 1.60 | 37 |

Body Surface area dependent Dose conversion: Rat (150 g) to Man (70 Kg) is 1/7 the rat dose. This means that in the present case 0.001-0.4 mg/Kg in rats equals to about 0.14-56 microgram/Kg in humans; assuming an average weight of 70 Kg, this would translate into an absolute dosage of about 0.01 to about 4 mg.

Conversion II:

The following conversion factors: Mouse=3, Rat=67. Multiply the conversion factor by the animal weight to go from mg/Kg to mg/m$^2$ for human dose equivalent.

| Species | Weight (Kg) | BSA (m$^2$) |
|---|---|---|
| Human | 70.00 | 1.710 |
| Mouse | 0.02 | 0.007 |
| Rat | 0.15 | 0.025 |
| Dog | 8.00 | 0.448 |

According to this equation the amounts equivalent to 0.001-0.4 mg/Kg in rats for humans are 0.16-64 μg/Kg; namely an absolute dose for a human weighing about 70 Kg of about 0.011 to about 4.4 mg, similar to the range indicated in Conversion I.

Conversion III:

Another alternative for conversion is by setting the dose to yield the same plasma level or AUC as that achieved following administration to an animal.

Thus, based on measurement made in mice following oral administration of IB-MECA (an $A_3AR$ agonist) and based on such measurements made in humans in a clinical study in which IB-MECA was given to healthy male volunteers it was concluded that a dose of 1 microgram/Kg-400 microgram/Kg in mice in which IB-MECA was effective and is equivalent to a human dose of about 0.14-57 microgram/Kg, namely a total dose for a 70 Kg individual of 0.01-4 mg.

Further, based on the above conversion methods, a preferred dosage range for IB-MECA and Cl-IB-MECA (another $A_3AR$ agonist) would be less than 4 mg, typically within the range of about 0.01 to about 2 mg (about 0.14-28 micrograms/Kg, respectively) and desirably within the range of about 0.1 to 1.5 mg (about 1.4-21 micrograms/Kg, respectively). This dose may be administered once, twice or at times several times a day.

Human studies as described in US patent application publication No. 20050101560 and by Fishman et al. [Fishman P. et al., Tolerability, pharmacokinetics, and concentration-dependent hemodynamic effects of oral CF101 (oral IB-MECA), an A3 adenosine receptor agonist, in healthy young men *Int J Clin Pharmacol Ther.* 42:534-542, 2004] showed that the level of IB-MECA decays in the human plasma with a half life of about 8-10 hours, as compared to a half life of only 1.5 hours in mice, in case of multiple daily administration, correction in the dosages for accumulative effects needs to be made at times (a subsequent dose is administered before the level of a previous one was decayed and thus, there is a build-up of plasma level over that which occurs in a single dose. On the basis of said human trials twice daily administration appears to be a preferred administration regiment. However this does not rule out other administration regiments.

In accordance with one embodiment of the invention, the administration of $A_3AR$ agonist is preferably daily administration, between once and a few times a day, preferably once or twice a day, the dose in each administration being in the range of between about 1 to about 1000 µg/kg body weight, preferably less than 400 µg/kg body weight, and even less than 200 µg/kg body weight. Typically, the dose of $A_3AR$ agonist is in a range of 1 to 100 µg/kg body weight.

The $A_3AR$ agonist is formulated in a pharmaceutical composition. A "composition" in the context of the invention is intended to mean a combination of the active agent(s), together or separately, with a pharmaceutically acceptable carrier as well as other additives. The carrier may at times have the effect of the improving the delivery or penetration of the active ingredient to the target tissue, for improving the stability of the drug, for slowing clearance rates, for imparting slow release properties, for reducing undesired side effects etc. The carrier may also be a substance that stabilizes the formulation (e.g. a preservative), for providing the formulation with an edible flavor, etc. For examples of carriers, stabilizers and adjuvants, see E. W. Martin, REMINGTON'S PHARMACEUTICAL SCIENCES, MacK Pub Co (June, 1990).

The term "pharmaceutically acceptable carrier" in the context of the present invention denotes any one of inert, non-toxic materials, which do not react with the $A_3AR$ agonist and which can be added to formulations as diluents, carriers or to give form or consistency to the formulation.

The composition of the present invention is administered and dosed in accordance with good medical practice, taking into account the clinical condition of the individual patient, the site and method of administration, scheduling of administration, patient age, sex, body weight and other factors known to medical practitioners. The choice of carrier will be determined in part by the particular active ingredient, as well as by the particular method used to administer the composition. Accordingly, there is a wide variety of suitable pharmaceutical compositions of the present invention.

The $A_3AR$ agonist may be administered to the subject by a variety of delivery modes as known in the art. It is preferable however that the $A_3AR$ agonist be administered orally. The carrier will be selected based on the desired form of the formulation.

Typical examples of carriers suitable for oral administration include (a) liquid solutions, where an effective amount of the $A_3AR$ agonist is dissolved in diluents, such as water, saline, natural juices, alcohols, syrups, etc.; (b) capsules (e.g. the ordinary hard- or soft-shelled gelatin type containing, for example, surfactants, lubricants, and inert fillers), tablets, lozenges (wherein the $A_3AR$ agonist is in a flavor, such as sucrose or the $A_3AR$ agonist is in an inert base, such as gelatin and glycerin), and troches, each containing a predetermined amount of A3AR agonist as solids or granules; (c) powders; (d) suspensions in an appropriate liquid; (e) suitable emulsions; (f) liposome formulation; and others.

The $A_3AR$ agonist may also be formulated for topical application. To this end, the $A_3AR$ agonist is combined with a physiologically acceptable carrier to obtain a cream, a lotion, an ointment, a gel, a hydrogel, a water-in-oil emulsion and the like, suitable for topical application, as known to those skilled in the art.

As noted above, the therapeutic use of an $A_3AR$ agonist may at times be in combination with other drugs such as methotrexate (MTX), steroids, NSAIDS, and others. In such a combination treatment the other drug and the $A_3AR$ agonist may be given to patients at the same time or at different times, depending on the dosing schedule of each of the drugs. MTX, for example, is typically given to patients once weekly at doses ranging between 5 and 25 mg, each weekly dose, either orally or parenterally. An $A_3AR$ agonist is typically given at a more frequent dosing schedule, for example once or twice daily.

The invention has been described in an illustrative manner, and it is to be understood that the terminology which has been used, is intended to be in the nature of words of description rather than of limitation. Obviously, many modifications and variations of the present invention are possible in light of the above teaching. It is therefore, to be understood that within the scope of the appended claims, the invention may be practiced otherwise than as specifically described hereinafter.

EXEMPLARY EMBODIMENTS

Example 1

The effect of IB-MECA (herein at times CF101) alone or in combination with MTX, on the proliferation of the human or rat fibroblast like synoviocytes (FLS) was tested. An effect on proliferation of FLS is suggestive of potential therapeutic effect in osteoarthritis.

Human FLS Cultures

Human synovial fluid samples were collected from osteoarthritis (OA) patients undergoing paracenthesis. The fluid was centrifuged and the supernatant removed. The cells were resuspended in DMEM containing type I collagenase (4 mg/ml), for 2 hours, and shacked vigorously at 37°. The released cells in the supernatant were harvested by centrifugation and were cultured in DMEM containing 10% FBS, 2 mM glutamine, 100 U/ml penicillin, 100 µg/ml streptomycin, 1% non essential amino acids, 1% sodium pyruvate and 20 nM HEPES buffer in a 37° C., 5% $CO_2$ incubator. After overnight culture, non-adherent cells were removed. The adherent cells (FLS) were subcultured at a 1:2 ratio, and the cells from passages 4 through 10 were used in the experiments.

The effect of CF101 alone or in combination with MTX, on the proliferation of the FLS was tested utilizing an MTT assay. The cells ($5 \times 10^4$/ml cells) were incubated in 96-well microtiter plates for 72 hours in the growth medium. At the last 24 hours CF101 (10 nM) were added to the cultures.

Rat Fibroblast Like Synoviocytes (FLS) cultures

Synovia tissue from adjuvant induced arthritis rats was collected. The tissue was minced and subjected for digestion in 4 mg/ml type I collagenase and 0.25 w/v trypsin in DMEM. The mixture was shacked vigorously for 4 hours at 37°. The released cells were separated from the supernatant by centrifugation and cultured in DMEM containing 15% FCS, 2 mM glutamine, 100 U/ml penicillin, 100 µg/ml streptomycin in a 37° C., 5% $CO_2$ incubator. After overnight incubation the nonadherent cells were removed. The adherent cells (FLS) were sub-cultured at a 1:2 ratio, and the cells from passages 4 through 10 were used in the experiments.

The effect of CF101 alone or in combination with MTX, on the proliferation of the FLS was tested utilizing an MTT assay. The cells ($5\times10^4$/ml cells) were incubated in 96-well microtiter plates for 72 hours in the growth medium. At the last 24 hours CF101 (10 nM) were added to the cultures.

Results

Figure 1A:
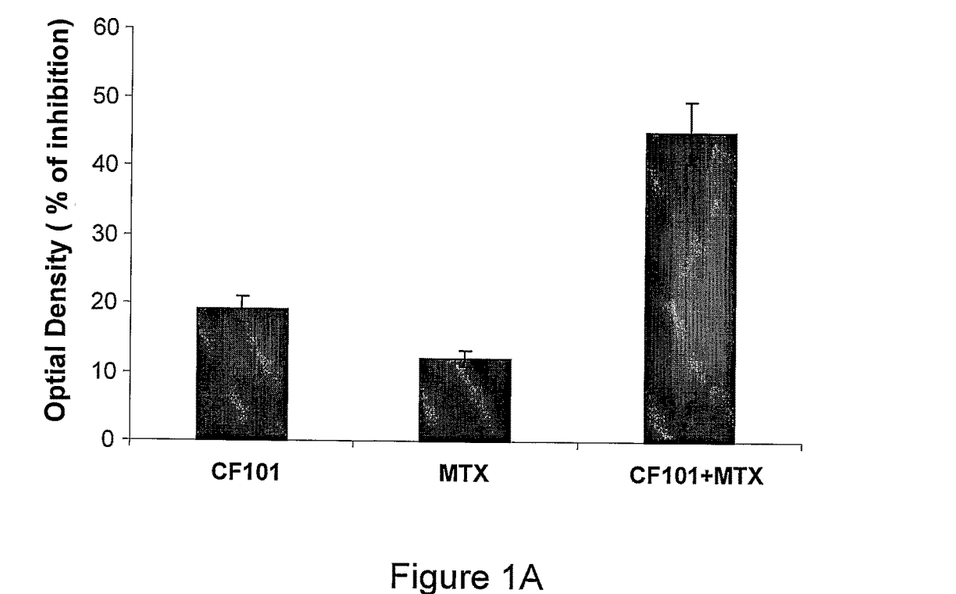
FIGS. 1A-1B are bar graphs showing the effect of treatment of IB-MECA (CF101) or a combined treatment of IB-MECA and MTX on the proliferation of human fibroblasts like synoviocytes (FLS) (FIG. 1A) or rat FLS (FIG. 1B) as determined by MTT assay.
Figure 1B:
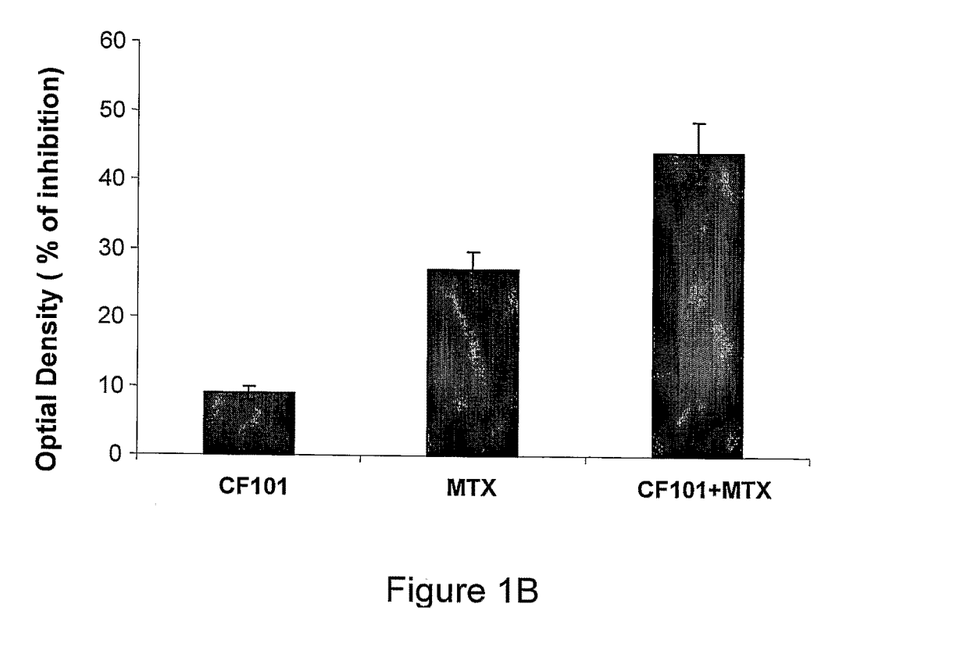

FIGS. 1A and 1B show, respectively, the effect of CF101 alone, MTX alone and a combination of CF101 and MTX on the proliferation of human and rat FLS, respectively, as evaluated by the MTT assay. As shown, the percent of inhibition as compared to control was significant (20% above control). As can clearly be seen, both CF101 alone or CF101 in combination with MTX exhibited a marked inhibitory effect on the FLS.

Example 2

In the following study the effect of IB-MECA (herein, at times, CF101) on the development of experimental osteoarthritis (OA) was determined. In this study the mono-idoacetate (MIA) experimental model was utilized. The MIA is a rat experimental model that rapidly reproduces the clinical and pathological characteristic of OA. MIA is an inhibitor of glycolysis which has been shown to induce chondrocyte death in vitro. Infra-articular injection of MIA induces chondrocyte death in the articular cartilage of rodent.

Specifically, male Wistar rats (~200 gr) (Harlan laboratories) were anesthetized with Isoflurane and the right leg was flexed at a 90° angle of the knee. The MIA was dissolved in physiological saline and 2 mg, at a volume of 50 μL were injected intra-articular of the right foot of each animal, using a 27-gauge, 0.5-inch needle.

Treatment with CF101, 100 μg/kg, Per Oz (PO), twice daily was initiated at day 7 post-injection.

Figure 2:
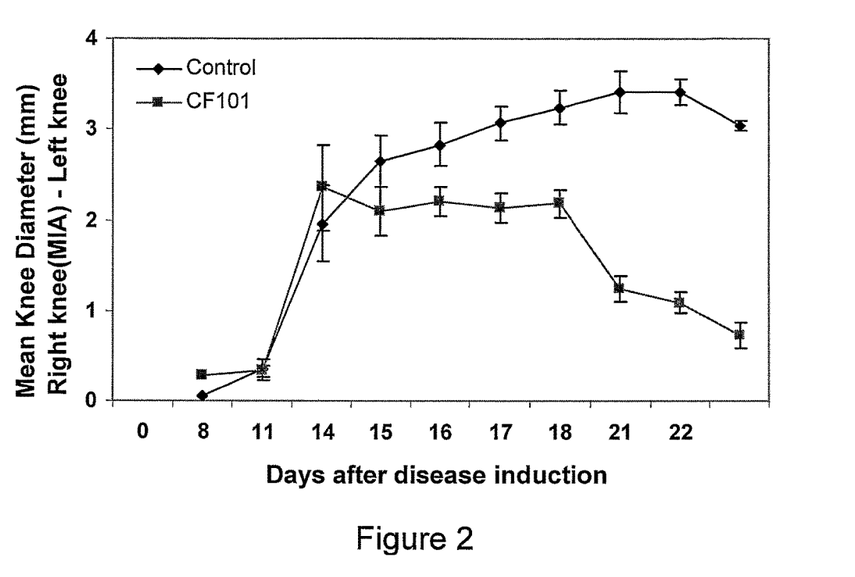
FIG. 2 is a graph showing the difference in diameter of MIA injected knee (Right knee) and diameter of the MIA un-injected knee (Left knee) within the same animal as a function of days after MIA induction, in CF101 treated (-■- CF101) and non treated (-♦- control). Each group contained 5 animals.

Knee diameter was measured using calibrated digital caliper adapted by reinforcing the tips for knee diameter measure. The results presented in FIG. 2 show the delta between the diameter of the MIA injected knee (Right knee) and the diameter of the MIA un-injected knee (Left knee) within the same animal. The group of the control is compared to the CF101 treated group (5 animals in each group).

As shown in FIG. 2, CF101 significantly inhibited the development of the tissue swelling in comparison to the control group (P=9.48317E-06).

Figure 3A:
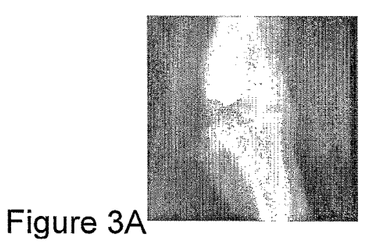
FIGS. 3A-3D are roentgenographic images of knees showing normal tibial epiphysial line without sclerosis in CF101 treated animals (FIGS. 3C and 3D, left and right knees respectively) as compared to vehicle treated animals (FIGS. 3A and 3B, left and right knees, respectively).
Figure 3B:
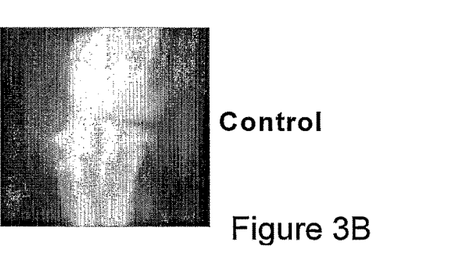
Figure 3C:
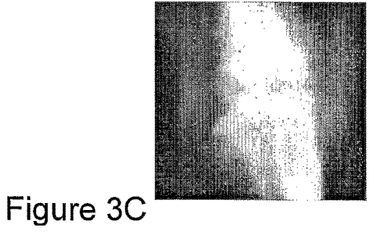
Figure 3D:
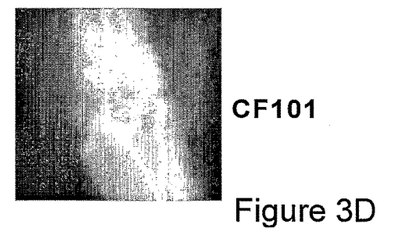
Figure 4A:
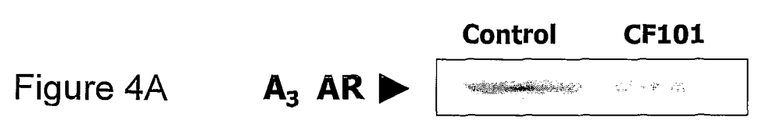
FIGS. 4A-4E are Western Blot analyses of protein extracts derived from CF101 treated (CF101) and non-treated (Control) knee joints of OA rats; the protein extracts being $A_3AR$ (FIG. 4A), PI3K (FIG. 4B), IKK (FIG. 4C), NF-κB (FIG. 4D), GSK-3β (FIG. 4E).
Figure 4B:
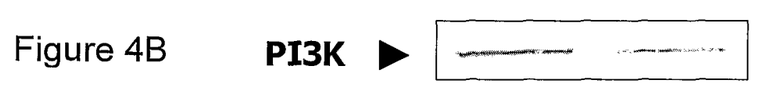
Figure 4C:
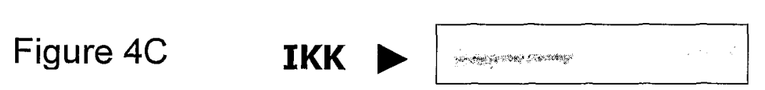
Figure 4D:
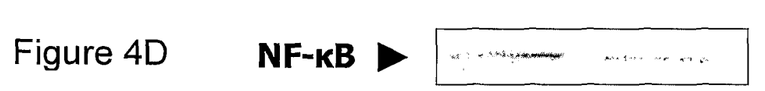
Figure 4E:
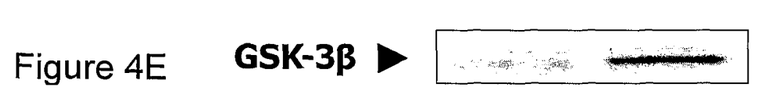

In addition roentgenographic examination of representative knees revealed sclerotic region adjacent to the tibial epiphysial line, thinning of the epiphysis and small exophite in the vehicle treated animals. In the CF101 treated animals normal tibial epiphysial line without sclerosis was noted (FIGS. 3A-3D, wherein FIGS. 3A and 3B represent the non-treated control group and FIGS. 3C and 3D represent the CF101 treated group).

To explore the fate of the $A_3AR$ and downstream key signaling proteins participating in the NF-kB and Wnt signaling pathways, knee joints protein extracts from control and CF101 treated animal were subjected to Western blot analysis. $A_3AR$ was highly expressed in cells extracted from the rat knee joints of the OA rats and down-regulated upon CF101 treatment, demonstrating that receptor activation took place. This was followed by down-regulation in the expression level of PI3K, IKK and NF-kB, indicating that upon treatment with CF101 the NF-kB signaling pathway was inhibited. Moreover, the expression level of GSK-3β, a key element of the Wnt signaling pathway, was up-regulated upon CF101 treatment (FIGS. 4A-4E).

This data thus clearly shows that CF101, a small orally bioavailable molecule capable of ameliorating inflammatory processes in the knee joints of OA subjects. The high $A_3AR$ expression level in the OA rats and the de-regulation of the NF-kB and Wnt signaling pathway induced by CF101 treatment strengthens the suggestion to utilize $A_3AR$ to combat OA.

The invention claimed is:

1. A method for treating osteoarthritis in a subject, comprising:
    administering to the subject in need thereof a therapeutically effective amount of an $A_3$ adenosine receptor agonist ($A_3AR$ agonist),
    wherein the therapeutically effective amount is an amount of from about 1 to about 100 μg/kg body weight.

2. The method of claim 1, wherein the subject is a human subject.

3. The method of claim 1, wherein administering comprises oral administration of the $A_3AR$ agonist to the subject in need thereof.

4. The method of claim 1, wherein administering comprises administration of the $A_3AR$ agonist to the subject once or twice daily.

5. The method of claim 1, wherein administering comprises administering the $A_3AR$ agonist in combination with an additional drug selected from the group consisting of methotrexate (MTX), a steroid and a non-steroidal anti-inflammatory drug (NSAID).

6. The method of claim 5, wherein the additional drug is methotrexate.

7. A method for treating osteoarthritis in a subject, comprising:
    administering to the subject in need thereof a therapeutically effective amount of 1-deoxy-1-{6[({3-iodophenyl} methyl)amino]-9H-purine-9-yl}-N-methyl-β-D-ribofuranuronamide (IB-MECA) and 2-chloro-$N^6$-(3-iodobenzyl)adenosine-5'-N-methlyuronamide (Cl-IB-MECA),
    wherein the therapeutically effective amount is an amount of from 0.16 to 64 μg/Kg body weight.

8. The method of claim 7, wherein the subject is a human subject.

9. The method of claim 7, wherein administering comprises oral administration of the $A_3AR$ agonist to the subject in need thereof.

10. The method of claim 7, wherein administering comprises administration of the $A_3AR$ agonist to the subject once or twice daily.

11. The method of claim 7, wherein administering comprises administering the $A_3AR$ agonist in combination with an additional drug selected from the group consisting of methotrexate (MTX), a steroid and a non-steroidal anti-inflammatory drug (NSAID).

12. The method of claim 11, wherein the additional drug is methotrexate.

13. A method for treating osteoarthritis in a subject, comprising:
    administering to the subject in need thereof a therapeutically effective amount of 1-deoxy-1-{6-[({3-iodophenyl} methyl)amino]-9H-purine-9-yl}-N-methyl-β-D-ribofuranuronamide (IB-MECA) and 2-chloro-$N^6$-(3-iodobenzyl)adenosine-5'-N-methlyuronamide (Cl-IB-MECA), wherein the therapeutically effective amount is an amount of less than 4 mg a day.

* * * * *